United States Patent
Pisklak et al.

(10) Patent No.: US 11,441,415 B2
(45) Date of Patent: Sep. 13, 2022

(54) MANAGING WELLBORE CEMENT COMPOSITIONS BASED ON MATERIAL CHARACTERISTICS

(71) Applicant: Halliburton Energy Services, Inc., Houston, TX (US)

(72) Inventors: Thomas Jason Pisklak, Cypress, TX (US); Samuel Jason Lewis, Jr., Spring, TX (US); John P. Singh, Kingwood, TX (US); Abraham S. Grader, Humble, TX (US); Ronnie Glen Morgan, Waurika, OK (US); Brendon C. Tan, Spring, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 360 days.

(21) Appl. No.: 16/629,076

(22) PCT Filed: Feb. 12, 2019

(86) PCT No.: PCT/US2019/017679
§ 371 (c)(1),
(2) Date: Jan. 7, 2020

(87) PCT Pub. No.: WO2020/167297
PCT Pub. Date: Aug. 20, 2020

(65) Prior Publication Data
US 2021/0207470 A1 Jul. 8, 2021

(51) Int. Cl.
*E21B 47/00* (2012.01)
*G01N 23/04* (2018.01)
(Continued)

(52) U.S. Cl.
CPC ......... *E21B 47/005* (2020.05); *G01N 23/046* (2013.01); *G01N 23/20091* (2013.01);
(Continued)

(58) Field of Classification Search
CPC ............... E21B 47/005; G01N 23/046; G01N 23/20091; G01N 23/223; G01N 23/2251; G01N 24/081; G01N 33/383
See application file for complete search history.

(56) References Cited

U.S. PATENT DOCUMENTS 5,253,719 A   10/1993   Blauch et al.
7,753,117 B2  7/2010    Ramakrishnan et al.
(Continued)

FOREIGN PATENT DOCUMENTS

WO   2018156124   8/2018

OTHER PUBLICATIONS

Iverson, et al. "Strength Retrogression In Cements Under High-Temperature Conditions", Proceedings, Thirty-Fifth Workshop on Geothermal Reservoir Engineering, Stanford University, Feb. 2010, pp. 8.
(Continued)

*Primary Examiner* — Mark R Gaworecki
(74) *Attorney, Agent, or Firm* — Kilpatrick Townsend & Stockton LLP (57) ABSTRACT

Wellbore cement compositions can be managed based on material characteristics determined from a cement sample. For example, a cement sample can be retrieved from a wellbore. The cement sample can be analyzed using a plurality of sensors to generate a three-dimensional mapping of particles in the cement sample. The three-dimensional mapping can represent three-dimensional spatial relationships between the particles in the cement sample. The three-dimensional mapping can be compared to baseline three-dimensional mappings in a database. The comparison of the three-dimensional mappings can be used to identify at least one material characteristic of the cement sample. Based on the at least one material characteristic of the cement
(Continued)

sample, a cement mixture can be prepared or information related to the cement mixture can be output.

20 Claims, 6 Drawing Sheets

(51) Int. Cl.
    *G01N 23/223*     (2006.01)
    *G01N 23/20*     (2018.01)
    *G01N 23/2251*     (2018.01)
    *G01N 24/08*     (2006.01)
    *G01N 33/38*     (2006.01)
    *E21B 47/005*     (2012.01)
    *G01N 23/046*     (2018.01)
    *G01N 23/20091*     (2018.01)

(52) U.S. Cl.
    CPC ....... *G01N 23/223* (2013.01); *G01N 23/2251* (2013.01); *G01N 24/081* (2013.01); *G01N 33/383* (2013.01)

(56) References Cited

U.S. PATENT DOCUMENTS

| | | |
|---|---|---|
| 8,590,382 B2 | 11/2013 | Zaleski, Jr. et al. |
| 9,201,026 B2 | 12/2015 | Walls et al. |
| 9,741,106 B2 | 8/2017 | Grader et al. |
| 9,746,431 B2 | 8/2017 | Grader et al. |
| 2011/0017447 A1 | 1/2011 | Zaleski, Jr. et al. |
| 2017/0205388 A1 | 7/2017 | Thomas et al. |
| 2017/0268325 A1 | 9/2017 | Draper et al. |
| 2018/0142544 A1* | 5/2018 | Kolchanov ............. G06F 30/20 |
| 2018/0329110 A1* | 11/2018 | Hu ........................... G01V 5/08 |

OTHER PUBLICATIONS

International Application No. PCT/US2019/017679, International Search Report and Written Opinion, dated Nov. 11, 2019, 13 pages.

* cited by examiner

MANAGING WELLBORE CEMENT COMPOSITIONS BASED ON MATERIAL CHARACTERISTICS

TECHNICAL FIELD

The present disclosure relates generally to systems and methods for use in a well system environment. More specifically, but not by way of limitation, this disclosure relates to managing wellbore cement compositions based on material characteristics.

BACKGROUND

As cement cures, its properties evolve over time. In many cases, the evolution of material characteristics of cement is rapid during the first few days, followed by a much slower rate that continues to decline over a period of years. Measuring material characteristics of cement can be time consuming and prone to errors, making measuring the evolution of material characteristics in a given sample difficult or inaccurate. Inability to determine how a cement mixture evolves within the wellbore can prevent an operator from verifying the integrity of downhole casings, such as a casing shoe and the area surrounding the casing shoe.

Determining time-dependent material characteristics of cement being cured downhole can be critical in determining the initial stress state of the cement once set, within the 4-hour to 7-day window of time. Without knowing how material characteristics of a cement mixture develop over time in a wellbore under actual downhole conditions, a large number of unknown factors can prevent an ideal cement composition from being implemented. This can increase the risk of the cement mixture failing to set. Inability for a cement mixture to set can cause failure within the wellbore, for example, by causing casing strings to fail as barriers, which in turn may cause blowouts and damage to existing downhole structures. Inability for a cement mixture to set in an adequate amount of time, as designed and planned, can cause non-productive time (NPT) and increase the cost and time for an operator to drill a well.

DETAILED DESCRIPTION

Certain aspects and features relate to a cement analysis system usable for managing wellbore cement compositions based on material characteristics. For example, the cement analysis system can include multiple sensors capable of analyzing a cement sample retrieved from a wellbore to identify the sample's material characteristics, which can define spatial, physicochemical, and mechanical properties of the sample. The cement analysis system can analyze the sample to generate a three-dimensional ("3D") mapping of the various characteristics of the sample, including time-dependent characteristics. The cement analysis system can also include a database of baseline 3D mappings for bulk blend components, crystalline phase, strength retrogression, and mechanical properties. Other analyzed cement samples can be used to build the database. The cement analysis system can compare the 3D mapping of the cement sample against baseline 3D mappings in the database (e.g., baseline 3D mappings that where generated using similar wellbore conditions) to determine one or more material characteristics of the cement sample, which may be indicative of how the cement sample's curing downhole. If the cement sample's material characteristics are unsuitable for a desired wellbore application, a condition within the wellbore can be changed or a composition of the cement being poured downhole can be made to reduce the chances of cement failure.

Some examples can provide systems and methods usable to verify the integrity of the wellbore cement, for example, that was deposited inside a casing shoe, using spatial, physicochemical, and mechanical methods. For example, the cement analysis system can verify that the quality of cement placed in the annular space between the casing shoe and the formation or another casing wall is equal to or better than the cement deposited inside the casing shoe. As another example, the cement analysis system can verify that an appropriate mixture of cement was deposited and set correctly within a wellbore to develop a dependable barrier within a certain timeframe. Three-dimensional analysis techniques can be used to develop a database of physical and chemical data of bulk blend ingredients useable to quantify the physical integrity and chemical composition of cement cuttings from drilling out a wellbore casing shoe after being cemented.

As used herein, "material characteristics" include physical properties, mechanical properties, chemical properties, and/or dimensional properties, all of which are distinct from one another. Examples of physical properties can include density, porosity, strength, permeability, calcium silicate hydrate (CSH) content in the cement sample, degree of crystallinity, volume fraction of a chemical component, surface area of particles, total surface area and average surface area of a chemical component, an amount of unreacted bulk blend component, Log-mean diameter (LMD), Log-mean standard deviation (LMSD), a given geometric shape factor of a chemical component in the cement sample, and four-dimensional coordinates of particles. Examples of mechanical properties can include compressive strength, tensile strength, Young's Modulus, Poisson's ratio, strain-to-failure, and American Society of Testing Materials (ASTM) toughness. Examples of chemical properties can include chemical composition, acidity, alkalinity, weathering, and corrosion. Examples of dimensional properties can include size and shape.

Conventional cement cuttings analysis techniques destroy the sample to determine the chemical properties of the cement, which prevents a spatial or temporal physicochemical analysis from being performed, thereby producing limited data. In contrast, some examples of the present disclosure enable the spatial and temporal physicochemical characteristics of a cement sample to be analyzed without destructive testing, providing a more complete picture as to how a specific slurry mixture sets within a wellbore with certain environmental conditions (e.g., temperature, pressure, time, etc.).

In some examples, the cement analysis system can develop 3D mappings for control samples of a given cement slurry that was prepared and cured under testing conditions (e.g., time, pressure, temperature) corresponding to the wellbore conditions downhole, such as wellbore conditions at the casing shoe when the casing shoe was drilled out. The composition of the control sample can be the same as slurry that was actually pumped into the wellbore (e.g., during cementing of a casing string). For example, the cement analysis system can apply multiple cement analysis techniques at the same time to build 3D spatial data maps of physical and chemical attributes of the control samples as they cure. A sample of the slurry actually pumped downhole can then be obtained from the wellbore and then analyzed using multiple sensors simultaneously to generate a 3D mapping that is comparable to the baseline 3D mappings of samples cured in the test environment. This comparison can establish relationships between expected material characteristics and actual material characteristics, which can help to better generate appropriate slurry mixtures for future cementing operations.

In some examples, the 3D mappings generated by the cement analysis system can be used to obtain accurate and appropriate time-dependent mechanical properties for curing a cement sample. By understanding the time-dependent mechanical properties of a cement sample, more reliable stress state measurements can be performed, and more reliable cement slurries can be designed by incorporating the initial stress state to existing models. This can allow for identification of the critical load bearing phases for a given slurry mixture. Using this information, it may be possible to design formulations with enhanced load bearing capacities, reducing the chance for wellbore failure due to cement setting failure.

Additionally or alternatively, the 3D mapping techniques can be used to measure and reduce strength retrogression in cement. Strength retrogression can occur above 230° F. (110° C.), at which point a cement mixture can experience a crystalline phase change (e.g., CSH gel turns into different crystals of varying shapes and volumes). In some examples, the cement analysis system can compare strength-retrogressed samples cured in a control environment against field samples to elucidate the actual amount of cement change occurring downhole, for example, in a cement sheath. In some examples, the cement analysis system can quantify phase change, porosity, and other physicochemical material changes in one measurement, all without damaging the structure of the sample. This can allow for real-time investigations during the phase change progression allowing for time-evolved elucidation of properties. The cement analysis system can analyze and catalogue this data into a database of structure property relationships, such as 3D mappings, to allow for rapid identification of structural weaknesses throughout phases of curing cement.

In some examples, the cement analysis system of the present disclosure can allow for the investigation of multiple cement compositions and determine which is most appropriate for the current downhole conditions. The database can further enhance the speed at which decisions for cement-composition selection are made. Correlating a cement sample from a wellbore to the designed cement composition and theoretical composition can allow for enhancements to slurry design. Verifying the downhole end state of the cement allows for more accurate initial cement-designs to reach the desired end properties. Knowing the material characteristics and time-dependent phase changes can allow for more engineered and tailored designs to meet the specific wellbore requirements to be assured of specific cement properties, resulting in reduction of remedial work caused by cement failure.

These illustrative examples are given to introduce the reader to the general subject matter discussed here and are not intended to limit the scope of the disclosed concepts. The following sections describe various additional features and examples with reference to the drawings in which like numerals indicate like elements, and directional descriptions are used to describe the illustrative aspects but, like the illustrative aspects, should not be used to limit the present disclosure.

Figure 1:
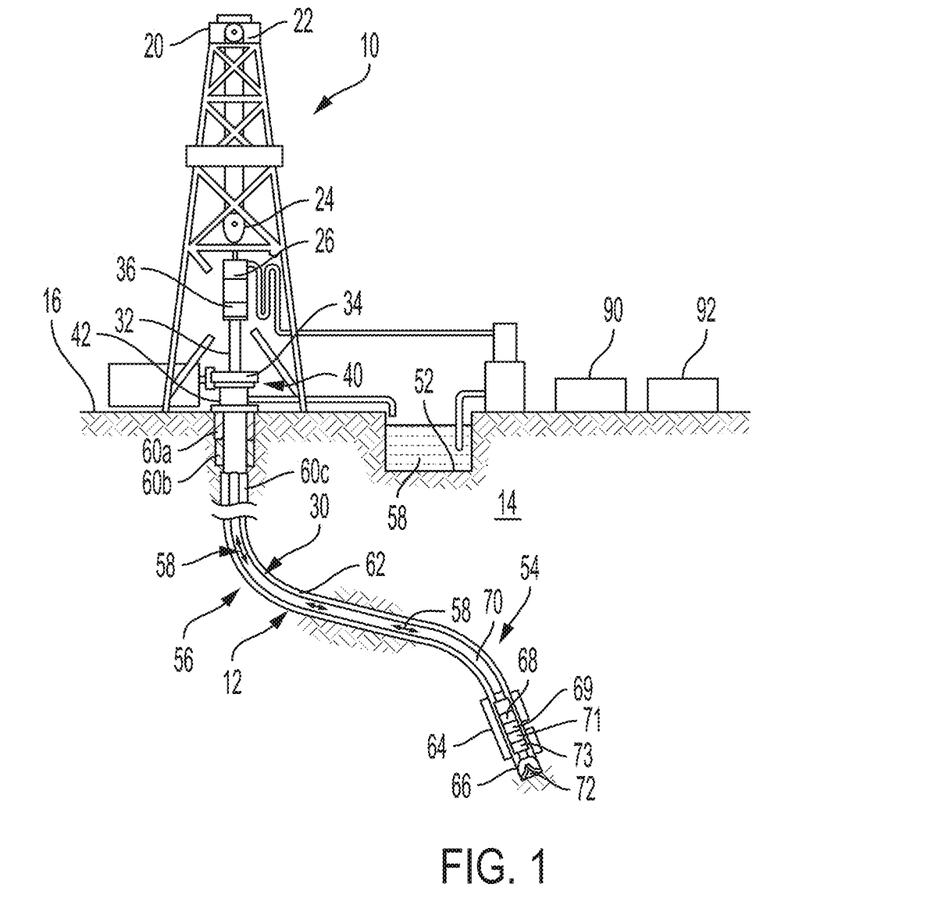
FIG. 1 is a cross-sectional view of an example of a well system incorporating a cement analysis system according to one aspect of the present disclosure.

FIG. 1 is a cross-sectional view of a well system 10 incorporating a cement analysis system 90 according to some examples of the present disclosure. The well system 10 can include a wellbore 12 extending through various earth strata in an oil and gas formation 14 (e.g., a subterranean formation) located below the well surface 16. The wellbore 12 may be formed of a single bore or multiple bores extending into the formation 14, and disposed in any orientation. The well system 10 can include a derrick or drilling rig 20. The drilling rig 20 may include a hoisting apparatus 22, a travel block 24, and a swivel 26 for raising and lowering casing, drill pipe, coiled tubing, and other types of pipe or tubing strings or other types of conveyance vehicles, such as wireline, slickline, and the like. The wellbore 12 can include a drill string 30 that is a substantially tubular, axially-extending drill string formed of a drill pipe joints coupled together end-to-end.

The drilling rig 20 may include a kelly 32, a rotary table 34, and other equipment associated with rotation or translation of drill string 30 within the wellbore 12. For some applications, the drilling rig 20 may also include a top drive unit 36. The drilling rig 20 may be located proximate to a wellhead 40, as shown in FIG. 1, or spaced apart from the wellhead 40, such as in the case of an offshore arrangement. One or more pressure control devices 42, such as blowout preventers (BOPs) and other well equipment may also be provided at wellhead 40 or elsewhere in the well system 10. Although the well system 10 of FIG. 1 is illustrated as being a land-based drilling system, the well system 10 may be deployed offshore.

A drilling or service fluid source 52 may supply a drilling fluid 58 pumped to the upper end of the drill string 30 and flowed through the drill string 30. The fluid source 52 may supply any fluid utilized in wellbore operations, including drilling fluid, cement slurry, acidizing fluid, liquid water, steam or some other type of fluid.

The well system 10 may have a pipe system 56. For purposes of this disclosure, the pipe system 56 may include casing, risers, tubing, drill strings, subs, heads or any other pipes, tubes or equipment that attaches to the foregoing, such as the drill string 30, as well as the wellbore and laterals in which the pipes, casing, and strings may be deployed. In this regard, the pipe system 56 may include one or more casing strings 60 cemented in the wellbore 12, such as the surface 60a, intermediate 60b, and other casing strings 60c shown in FIG. 1. An annulus 62 is formed between the walls of sets of adjacent tubular components, such as concentric and non-concentric casing strings 60 or the exterior of drill string 30 and the inside wall of the wellbore 12 or the casing string 60c.

Where the subsurface equipment 54 is used for drilling and the conveyance vehicle is a drill string 30, the lower end of the drill string 30 may include a bottom hole assembly 64, which may carry at a distal end a drill bit 66. During drilling operations, a weight-on-bit is applied as the drill bit 66 is rotated, thereby enabling the drill bit 66 to engage the formation 14 and drill the wellbore 12 along a predetermined path toward a target zone. In general, the drill bit 66 may be rotated with the drill string 30 from the drilling rig 20 with the top drive unit 36 or the rotary table 34, or with a downhole mud motor 68 within the bottom hole assembly 64.

The bottom hole assembly 64 or the drill string 30 may include various other tools, including a power source 69, mechanical subs 71 such as directional drilling subs, and measurement equipment 73, such as measurement while drilling (MWD) or logging while drilling (LWD) instruments, sensors, circuits, or other equipment to provide information about the wellbore 12 or the formation 14, such as logging or measurement data from the wellbore 12.

Measurement data and other information from the tools may be communicated using electrical signals, acoustic signals, or other telemetry that can be received at the well surface 16 to, among other things, monitor the performance of the drill string 30, the bottom hole assembly 64, and the associated drill bit 66, as well as monitor the conditions of the environment to which the bottom hole assembly 64 is subjected (e.g., drilling fluid 58 flow rate).

The drilling fluid 58 may be pumped to the upper end of drill string 30 and flow through a longitudinal interior 70 of the drill string 30, through the bottom hole assembly 64, and exit from nozzles formed in the drill bit 66. At the bottom end 72 of the wellbore 12, the drilling fluid 58 may mix with formation cuttings, formation fluids (e.g., fluids containing gasses and hydrocarbons) and other downhole fluids and debris. The drilling fluid mixture may then flow upwardly through an annulus 62 to return formation cuttings and other downhole debris to the well surface 16.

After drilling through a portion of the formation 14, the drill string 30 can be removed from the wellbore 12 and casing string 60c can be conveyed downhole to protect or isolate a portion of the formation 14 adjacent to the wellbore 12. Often, drilling a well can involve drilling in sections, with each well section being sealed off by lining the inside of the wellbore 12 with the casing string 60c and filling the annulus 62 between the casing string 60c and the inner wall of the wellbore 12 with cement.

Once the cement is set, or cured, the drill string 30 can then be used to drill through a casing shoe to reach a section of the formation 14 at a lower depth. Drilling through the casing shoe may occur after the cement holding the casing string 60c in place is partially or fully cured. As the drill string 30 drills through the casing shoe, the drilling fluid 58 can flush cement cuttings up toward the well surface 16 through the annulus 62 between the drill string 30 and the cemented casing string 60c. These cuttings can be collected using cutting screens, which separate the cuttings from the drilling fluid 58 at the well surface 16.

In some examples, the cement analysis system 90 can analyze samples of these cuttings using one of more sensors 92 to generate 3D mappings of the particles within the cutting samples. The 3D mappings can indicate various material characteristics of the cuttings. The cement analysis system 90 can compare the 3D mapping of the cutting sample to baseline 3D mappings in a database to determine if the 3D mapping of the cutting sample matches any of the baseline 3D mappings in the database. The baseline 3D mappings may have known material characteristics. In some examples, the baseline 3D mappings are generated by analyzing test slurries (e.g., cured in a laboratory) that were exposed to equivalent downhole conditions as the cuttings, since the material characteristics of the cuttings are dependent on the wellbore environmental conditions, such as temperature and pressure, and time. If the 3D mapping of the cutting sample matches one of the baseline 3D mappings in the database, then the cement analysis system 90 can attribute the known material characteristics associated with the baseline 3D mapping to the cutting sample. In some examples, the cement analysis system 90 can then alert a well operator of the cutting sample's material characteristics, so as to enable the well operator to take action (e.g., corrective action) based on the cutting sample's material characteristics.

Figure 2:
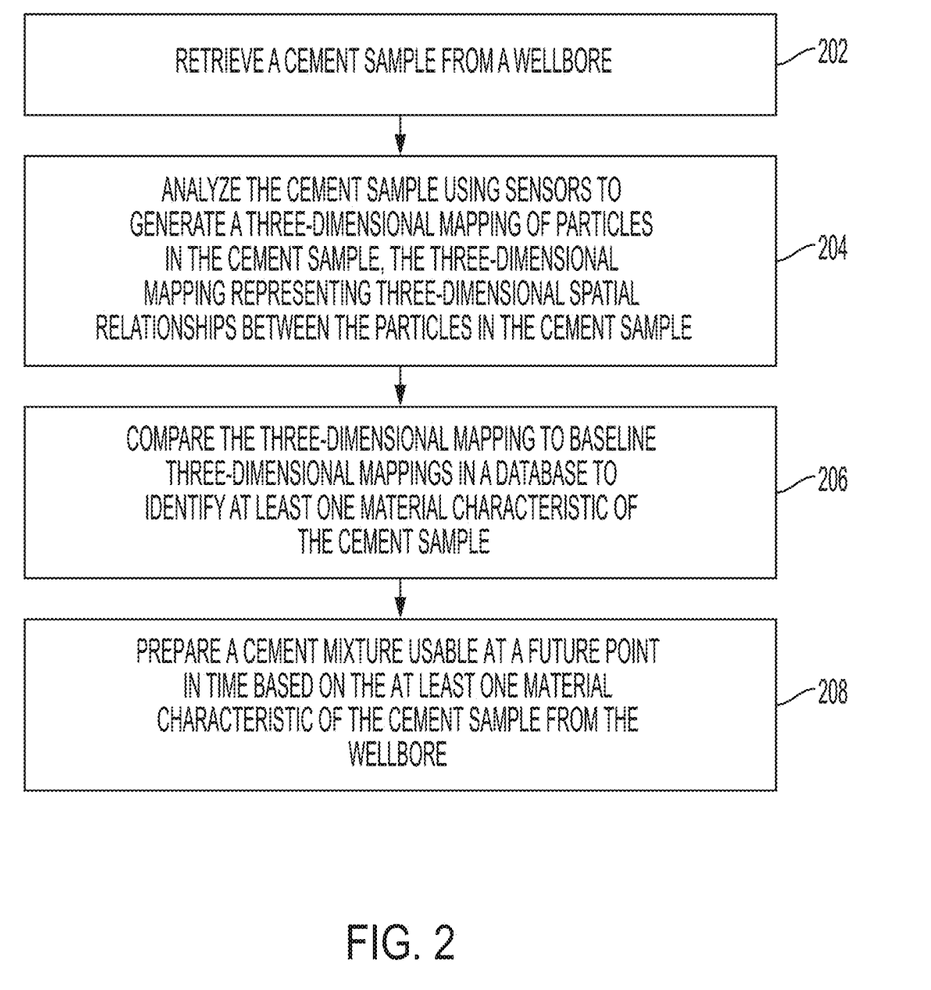
FIG. 2 is a flowchart describing a process for managing wellbore cement compositions based on material characteristics according to one aspect of the present disclosure.

FIG. 2 is a flowchart describing a process for managing wellbore cement compositions based on material characteristics according to some examples of the present disclosure. Some or all of the steps shown in FIG. 2 can be implemented using the cement analysis system 90 of FIG. 1.

Generally, a cement sample can be analyzed to generate a 3D mapping of the particles in the cement sample. The 3D mapping can be compared to baseline 3D mappings to identify a material characteristic of the cement sample. Based on the identified material characteristic of the cement sample from the wellbore, a cement mixture can be prepared. This cement mixture can then be used at a future point in time within the same wellbore from which the cement sample was taken or another wellbore. More specific details are discussed below.

In block 202, a cement sample is retrieved from a wellbore. The cement sample may include drill cuttings from a casing shoe or other cement obtained from other well locations. The cement sample can be a size large enough to represent an average homogeneity of the cured cement in the wellbore (e.g., a volume of 300 microns cubed). For example, a slurry mixture poured to form a casing shoe can be composed of a variety of bulk blend component mixed together. These bulk blend components chemically interact with each other to create reaction products which then form the set cement over time. The resulting set cement can have a similar consistency throughout the casing shoe, such that any given sample of drill cuttings can showcase a representative amount of bulk blend components used in the slurry mixture. Thus, a sample from one drill cutting from the casing shoe can have equivalent material characteristics as another sample from another drill cutting from the casing shoe.

Bulk blend components are raw materials that can be combined together to form a slurry having a certain composition, where the composition can affect the material characteristics of the resulting set cement. Bulk blend components can refer to unreacted materials, such as, but not limited to, Portland cements, volcanic ash, natural glasses, pozzolans (natural or man-made), cement kiln dust ("CKD"), Silica, CSH, calcium aluminum silicate hydrate ("CASH"), and ettringite. Using the cement analysis techniques discussed above, a 3D mapping for each type of bulk blend component can be determined. For example, Silica can have a 3D mapping representing different material properties than a 3D mapping for CSH.

The bulk blend components can produce reaction products, or phases, that form in the cement over time. A phase can refer to the physical organization of particles. Examples of phases can be an amorphous phase or crystalline phase. As bulk blend components are mixed together, they can chemically react to produce reaction products that can be analyzed over time by applying the various cement analysis techniques at different times during the curing process. The formation of reaction products may not be instantaneous, and may exhibit different structural and chemical properties throughout the curing process. For example, Portland cement and water can be mixed together to form CSH, or pozzolan and lime can be mixed together to form CSH. Both mixtures can result in the formation of CSH, but may produce different reaction product structures and/or different amounts of reaction products throughout the curing process. For example, one mixture may have more CSH or CASH or less ettringite than another mixture based on the bulk blend components used and the ensuing chemical reactions. The cement analysis system 90 can analyze the differences in reaction products throughout the curing process to produce different 3D mappings useable to form a comprehensive database, which enables the cement analysis system 90 to better map the curing process and temporal properties of a cement sample.

In block 204, the cement sample is analyzed using sensors to generate a 3D mapping of particles in the cement samples. The 3D mapping can represent 3D spatial and physico-chemical relationships between the particles in the cement sample.

Various sensors can be used to analyze the material characteristics of a cement sample. In some examples, the sensors can perform X-Ray Computing Tomography ("CT"), Focused Ion-Beam Scanning Electron Macroscopy ("FIB-SEM") with X-Ray Diffraction ("XRD"), X-Ray Fluorescence ("XRF"), Energy Dispersive Spectroscopy ("EDS"), Nuclear Magnetic Resonance ("NMR"), or any combination of these, on a cement sample in a sequential or concurrent manner. These analysis techniques will hereinafter be referred to as "cement analysis techniques." In some examples, the sensors can be components of the cement analysis system 90, which can execute test software that integrates the outputs from the sensors to form the 3D mapping of the cement sample. In some examples, the sensors can be separate components from the cement analysis system 90, such as downhole sensors or components of separate measurement devices, communicatively coupled to the cement analysis system 90. The cement analysis system 90 can communicate with the sensors to receive information about the material characteristics from the sensors.

The cement analysis system 90 and accompanying test software can be trained or otherwise calibrated to identify and measure material characteristics of cement samples. For example, the cement analysis system 90 can generate baseline 3D mappings by analyzing bulk blend components and set-cement slurry samples using the various cement analysis techniques. The cement analysis system 90 can then store these baseline 3D mappings in a database and use them for future comparisons when analyzing a specific cement sample from downhole (e.g., to determine, what, if any, changes to the slurry being pumped downhole should be made).

The 3D mappings related to the reaction products can be stored as separate 3D mappings, which may be associated with the corresponding 3D mappings for each type of reacted bulk blend component that makes up the set cement. For example, a 3D mapping corresponding to Silica and a 3D mapping corresponding to pozzolan can be stored in the database, and a separate 3D mapping for the reaction product between fine Silica and pozzolan can be stored in the database separately but in association with the 3D mappings for the two bulk blend components. In some examples, analysis data related to the reaction products can be a component of an overall 3D mapping associated with one or more bulk blend components.

In some examples, the cement analysis system 90 can analyze the individual bulk blend components and their reaction products to form accurate predictive models usable to predict phase changes during the cement curing process. For example, knowing the amount of a bulk blend components used in a mixture can help determine how the different amounts of bulk blend components can react with each other to produce the resulting cured cement. For example, a mixture may have an undesirably high amount of one bulk blend component that may create pockets of unreacted bulk blend components, such that the pockets prevent some of the excess bulk blend components from physically contacting and reacting with other bulk blend components. In this example, pockets of unreacted bulk blend components can create a structural weakness in the set cement, causing failure of the casing string. By understanding the material characteristics between bulk blend components and their corresponding reaction products, structural weaknesses of some slurry compositions can be anticipated through modeling, and therefore avoided.

In addition to 3D mappings for bulk blend components and their reaction products, the cement analysis system 90 can store baseline 3D mappings which can be used to further calibrate the cement analysis system 90 for each crystalline phase in set cement. The cement analysis system 90 can analyze cement samples from set cement slurries having different compositions (e.g., cement slurries used in different applications or multiple wellbores having varying downhole conditions) using the cement analysis techniques to further develop the database to include baseline 3D mappings for each crystalline/semi-crystalline phase (e.g., CSH, CASH, ettringite, etc.) in set cement. As more samples are compared to the 3D mapping base line database, the base line database may be expanded on a continuing basis. The composition matrix of a sample of set cement can be analyzed to determine how each bulk component used in the mixture interacts with each other over time to produce the set cement. The baseline 3D mappings for each sample of set cement stored in the database can be used as reference points that enable the cement analysis system 90 to analyze a new, unknown sample.

In some examples, the cement analysis system 90 can determine time-dependent material characteristics of a cement sample using 3D mappings for bulk blend components, phases, and strength retrogression along with known material characteristics. Once the various phases including the porosity have been identified, estimation of the material characteristics of the bulk blend components may be achieved by developing a structural model of the solid phase. As the material characteristics of the individual phases are obtained, 3D mappings of cement samples with single bulk blend components such as Portland, Fly Ash, pozzolan, etc., averaged or bulk properties for the cement sample may be calculated using structural modeling techniques. For example, single or pure versions of bulk blend components (e.g., Portland cements, Fly Ash, pozzolans, CKD, or other supplementary cementing materials with and without lime balance) balanced over calcium oxide ("CaO") can be prepared and analyzed by the cement analysis system 90 to generate 3D mappings throughout the curing process followed by material characteristic measurements. The cement analysis system 90 can couple the measured material characteristics with the 3D mappings to predict the material characteristics over time.

In some examples, the cement analysis system 90 can apply one or more of the following mathematical expressions to correlate the 3D mappings to the development of mechanical properties over time for a corresponding slurry mixture:

$$CS_{blend\ of\ n\ components} = f_{v,i}(CS_i)^{\alpha_i} + f_{v,i+1}(CS_{i+1})^{\alpha_{i+1}} \ldots f_{v,n}(CS_n)^{\alpha_n}$$

Where:

$f_{v,i}$ = volume fraction of phase i $CS_i$ = Compressive strength of phase i: note there will be $CS_i$ data for lime balance and as—is (without balancing lime)

$\alpha_i$ = specific coefficients for a given material $$YM_{blend\ of\ n\ components} = f_{v,i}SF_i(YM_i)^{\beta_i} + f_{v,i+1}SF_{i+1}(YM_{i+1})^{\beta_{i+1}} \ldots f_{v,n}SF_n(YM_n)^{\beta_n}$$

$SF_i$ = Shape Factor (SF) of phase i: note there will be $SF_i$ data for lime balance and as well as without lime balancing.

$YM_i$ = Young's Modulus of phase i: note there will be $YM_i$ data for lime balance and as well as without lime balancing.

$\beta_i$ = specific coefficients for a given material

Where:

$$SF_i = \frac{\text{Surface Area of individual particle of given crystalline species}}{\text{Volume of same}}$$

Using one or more of the techniques described herein, time-dependent material characteristics can be determined for different types of cement including, but not limited to, Portland cements, Low Portland cements, geopolymer cements, sorrel cements, resin cements, and pozzolanic cements. The time-dependent material characteristics can be stored in the database to enable the cement analysis system 90 to make future comparisons.

Figure 3:
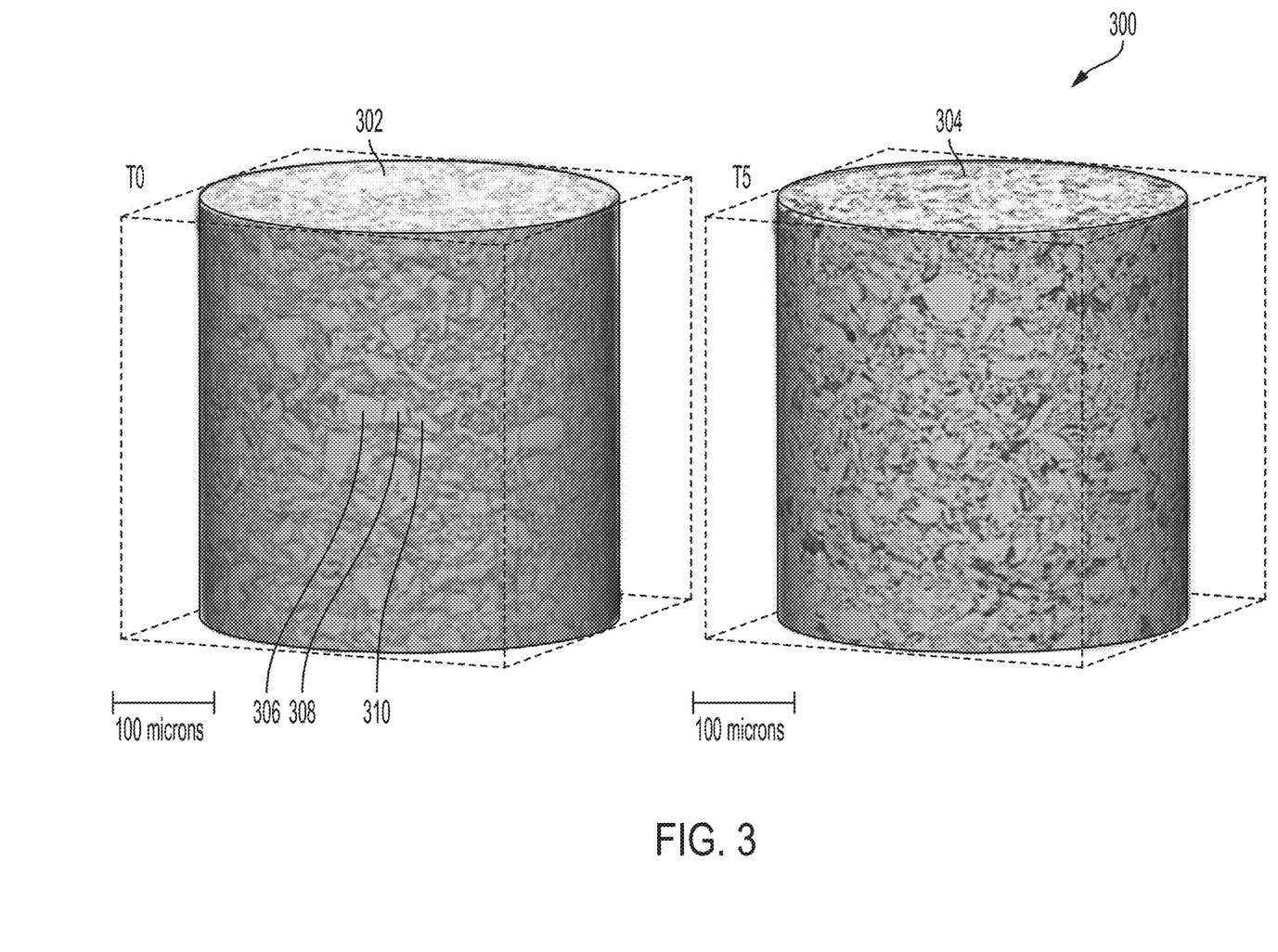
FIG. 3 depicts three-dimensional ("3D") mappings of cement samples at different points in time during a curing process according to one aspect of the present disclosure.

As mentioned above, the cement analysis system 90 can use cement analysis techniques that produce a 3D mapping without disturbing the structural integrity of the sample. For example, FIG. 3 depicts 3D mappings of cement samples at different points in time during a curing process according to some examples of the present disclosure. A sample can be associated with multiple 3D mappings corresponding to different time stamps in the curing process, where each time stamp can comparatively depict the progression of bulk-blend component reactions throughout the curing process.

More specifically, FIG. 3 depicts a 3D mapping 302 of a slurry mixture at timestamp zero, which corresponds to the instant the slurry mixture is mixed or pumped downhole before reaction and hardening occurs. The volume of the slurry mixture can be filled completely with various bulk blend components and/or water to dehydrate the bulk blend components. FIG. 3 also depicts another 3D mapping 304 of the same slurry mixture at timestamp five, which can be after the curing process is completed. Not shown in FIG. 3 are additional 3D mappings corresponding to other timestamps in between time zero and time five. A 3D mapping of partially-cured or fully-cured cement can illustrate material characteristics for each specific mixture. The material characteristics can include but not limited to physical properties, mechanical properties, chemical properties, and/or dimensional properties, as described previously.

The 3D mapping can depict material characteristics for each individual particle corresponding to a bulk blend component or a reaction product. Every particle can be attributed a numerical index that identifies the particle (e.g., distinguishes it from the other particles in the cement sample). For example, the slurry mixture can be analyzed at time zero to identify each particle within the sample volume, including particles 306, 308, 310. The particles 306, 308, 310 can be of the same chemical type and attributed an index of i=1, i=2, and i=3 respectively. The particles 306, 308, 310 can be tracked as the slurry mixture cures, and can be identified in the set cement of the slurry mixture at time-stamp five to analyze how the particles reacted over time. Values for volume, surface area, and total surface area can be given for each of the particles 306, 308, 310 referenced by the numerical index (e.g., (volume, i), (surface area, i), (total surface area, i)). The same mapping can be performed for reaction products, such as CSH, $SiO_2$ ("silicon dioxide"), CaO, or $Al_2O_3$, ("aluminum oxide") for partially and fully-cured slurries. Reaction products can also be mapped within a 3D mapping to determine additional parameters including average surface area, Log-mean diameter ("LMD"), Log-mean standard deviation ("LMSD"), and four-dimensional coordinates (e.g., x, y, z, and time coordinates).

Figure 4:
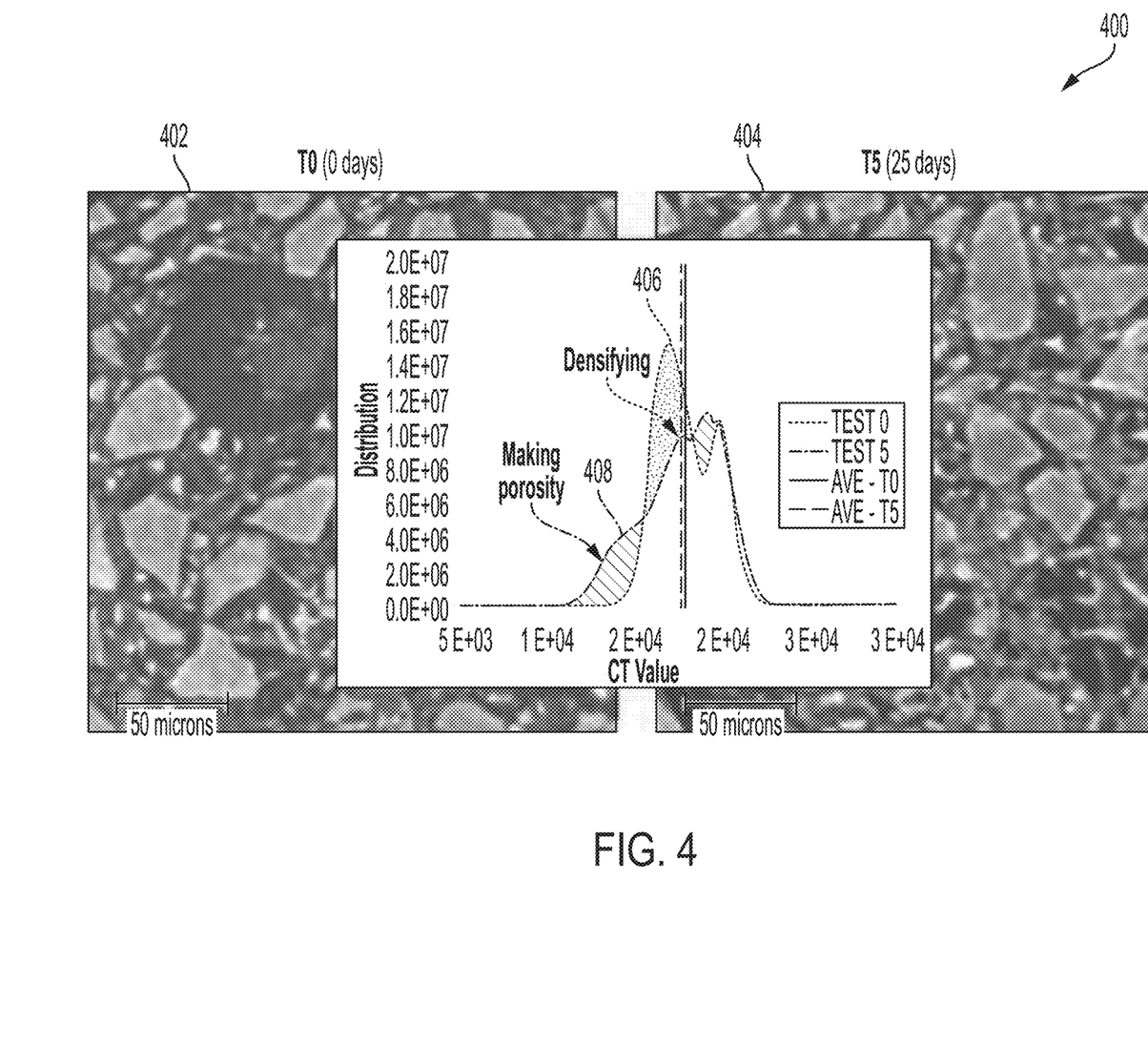
FIG. 4 depicts a graphical representation of material characteristics of cement throughout a curing process according to one aspect of the present disclosure.

To further describe the particle-to-particle relationships measureable by the cement analysis system 90, FIG. 4 depicts a graphical representation 400 of material characteristics of cement throughout a curing process according to some examples of the present disclosure. The left image 402 illustrates material characteristics of a slurry mixture at a time of zero days, and the right image 404 illustrates the resulting set cement at a time of 25 days. The graph in between the left image 402 and the right image 404 compares material properties of the slurry mixture at zero days to material properties of the set cement at 25 days. The line 406 illustrates the distribution of particles of the slurry mixture, and the line 408 illustrates the distribution of particles of the set cement. As the slurry mixture progresses through the curing process, it begins to densify and become more porous as the bulk blend components are dehydrated to form reaction products. The result of the curing process is a volume that is denser and more porous than the initial slurry mixture. The cement analysis system 90 can analyze the curing process over time to quantify of material characteristic changes for each particle within the sample volume.

Referring back to block 204 of FIG. 2, after calibrating the cement analysis system 90, a cement sample can be analyzed in a similar manner as the baseline set-cement slurry samples used to calibrate the cement analysis system 90. For example, the cement sample retrieved in block 202 can be analyzed to determine one or more 3D mappings of the cement sample. In one such example, a separate 3D mapping can be determined for each bulk component within the cement sample, and for each crystalline phase in the set cement, as previously described. Based on the multiple 3D mappings determined by the cement analysis system 90 for the specific cement sample being tested, a spatial signature for volume, surface area, total surface area, average surface area, LMD, LMSD, and/or four-dimensional coordinates can be determined for each bulk blend component and crystallized phase for the cement sample.

The 3D mappings of the bulk components and 3D mappings of the crystalline phases can be determined sequentially or simultaneously by the cement analysis system 90. For example, the cement analysis system 90 can apply any combination of the cement analysis techniques to determine a 3D mapping of bulk blend components and 3D mappings of crystalline phases at the same time and without disturbing the structure of the cement sample, preventing a need to separate the sample into its corresponding bulk blend components and/or reaction products. This can ensure that the cement sample can be used during additional testing when, for example, the cement sample is not fully cured and again when the cement sample is fully set, thereby enabling the same sample to be repeatedly analyzed over time.

In some examples, the cement analysis system 90 can apply the same techniques used to generate the 3D mappings reflecting the material properties of a cement sample to additionally or alternatively generate reaction maps of cements. Reaction maps can illustrate the chemical reactions for reaction products that occur during the cement curing. By mapping the chemical reactions between bulk blend components throughout the curing process, a baseline of how reaction products develop over time can be determined. A cured cement sample can have fully reacted reaction products. The cement analysis system 90 can use these reaction maps to analyze the reaction products of a cement sample in order to determine what bulk blend components were used in the original slurry mixture of the cement sample.

In block 206, the cement analysis system 90 compares the 3D mapping of the cement sample to baseline 3D mappings in a database to identify at least one material characteristic of the cement sample. After mapping the cement sample as described in block 204, the 3D mapping of the cement sample can be compared to a database containing multiple baseline 3D mappings. Based on the comparison, at least one material characteristic of the cement sample can be identified. In some examples, the cement analysis system 90 can determine that one or more of the identified material characteristics are negatively affecting the structural integrity of the downhole cement, and therefore increasing the chance of cement setting failure.

For example, the database can include baseline 3D mappings for a previously taken cement sample (e.g., from another wellbore as described in block 204) having the same bulk blend composition that was successfully set under the same or similar downhole conditions as are present in the current wellbore. An analysis of the cement sample being tested may show that the density of the cement sample is less than the density illustrated by the 3D mapping for the successfully set cement sample, where the density of the 3D mapping would be an expected value. The 3D mappings in the database can correspond to a target density having a threshold target density range, such as 13.8 pounds per gallon ("ppg") (1.65 t/m$^3$) +/−0.5 ppg (0.6 t/m$^3$). The cement analysis system 90 can then determine if there is a density disparity between the tested value and expected value. If the tested value of the cement sample falls outside the threshold density range, some remedial action may be taken, as described in greater detail below with reference to block 208. Alternatively, if the tested value is identical or within the target density threshold, then the well operator can be confident in the structural integrity of the cement downhole. Thus, the comparison can provide assurance that the sampled cement has successfully set, and no remedial action may be needed.

In some examples, a design of experiment can be generated and related information can be stored in the database. The design of experiment can include a range of cement designs to which varying temperatures, pressures, and time values corresponding to real world applications can be applied. These can be tested using the cement analysis system 90 and compared to actual cement samples corresponding to each cement design (obtained from actual wellbore applications) in order to validate the design of experiment for each cement design. Validating the design of experiment with actual measurements for each cement design can refine calibration of the database for use in subsequent comparisons of 3D mappings.

Figure 5:
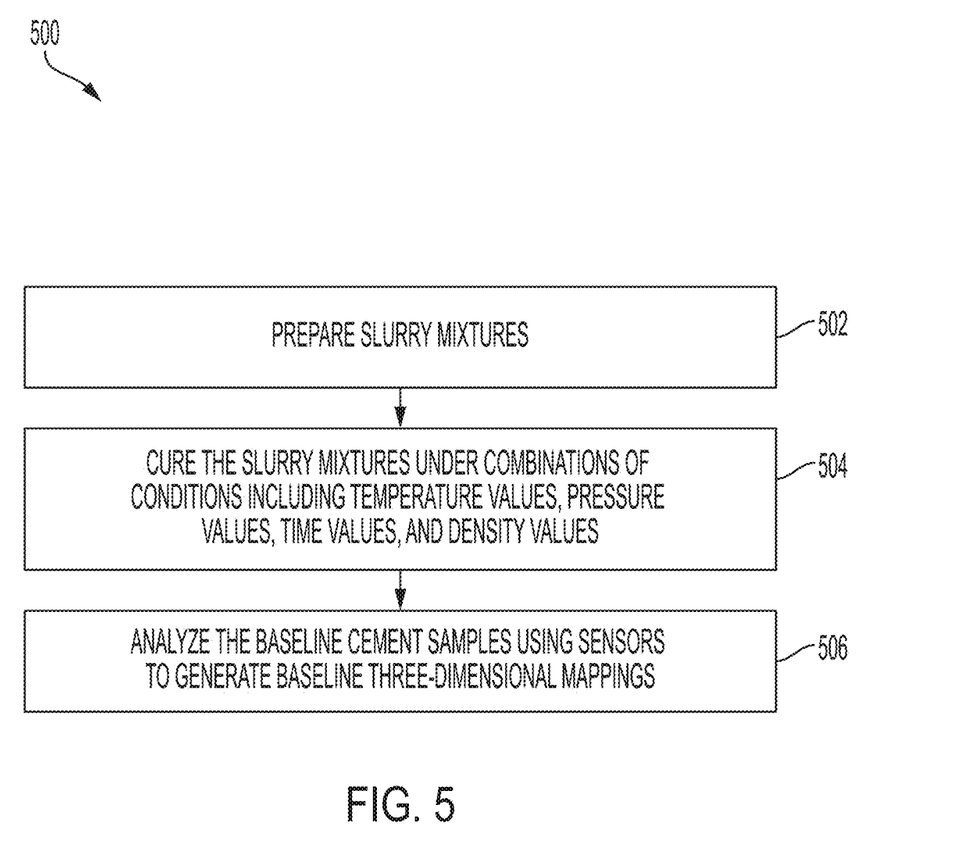
FIG. 5 is a flowchart describing a process for developing baseline three-dimensional mappings according to one aspect of the present disclosure.

In some examples, the database used for comparison against a cement sample as described in block 206 can be generated according to the flowchart depicted in FIG. 5. Similar to examples where the 3D mapping of the cement sample being tested is matched against baseline 3D mappings of cement samples previously taken (e.g., from other wellbores) to build the database, methods can be used to match a 3D mapping of the cement sample being tested against baseline 3D mappings of control samples. Control samples can include samples of slurries prepared and cured in a controlled environment. For example, a slurry mixture equivalent to the cement sample being tested can be prepared in a control environment and cured under the same environmental and time conditions present within the wellbore. Comparing 3D mappings of the cement sample to the 3D mappings of the control cement samples having similar material compositions, and that were subjected to similar environmental conditions, can provide insights about whether the downhole cement has set successfully. In some instances, the 3D mappings for control samples can be built based on various contamination levels of mud and spacer and used to reverse engineer the estimated levels of contamination in cuttings from the drilled out casing shoe.

In block 502, slurry mixtures are prepared. The slurry mixtures can include any composition of bulk blend components that could be used in any application in setting cement downhole. Multiple slurry mixtures corresponding to a given composition of bulk blend components can be prepared, such that each mixture having the same composition may be subjected to different environmental conditions (e.g., in block 504) to determine 3D mappings for many or all possible mixture combinations under many or all possible wellbore conditions. In some examples, slurry mixtures can be prepared based on the suspected or actually-measured environmental conditions within a wellbore from which the cement sample will eventually be retrieved, as described in block 202 of FIG. 2. This can allow for cement slurries to be prepared in advance of being poured downhole eliminating the need for an analysis of the cement sample in hindsight.

In block 504, the slurry mixtures are cured under combinations of conditions including temperature, pressure, time, and/or density values to create baseline cement samples. The control samples can be cured under environmental conditions corresponding to the conditions and within a same timeframe as the cement sample from the wellbore. Downhole or surface sensors can be used to measure temperature and other downhole conditions as the cement is being poured and set downhole. And software can be used to predict temperature, pressure, and other wellbore condition values at various times throughout the curing process and at various depths in the wellbore. By subjecting the control samples to the same (or similar) conditions existing in a wellbore as determined by the sensors or predictive software, a determination of the structural integrity and a setting success rate of the cement sample can be determined by analyzing the material characteristics of the control samples.

In some examples, 3D mappings can be created for a range of density differences by changing water content of the control slurries. In some examples, the control samples can be cured at temperatures greater than or equal to 230° F. (110° C.), which can correspond to downhole temperatures at which the strength of the cement at the casing shoe begins to retrogress.

In block 506, the cement analysis system 90 analyzes the control cement samples using the sensors to generate baseline 3D mappings. The baseline 3D mappings can be compared against the 3D mapping of a cement sample retrieved from downhole, as described above with reference to block 206 of FIG. 2. The control cement samples can be analyzed using the cement analysis techniques as described in examples.

Relationships between material characteristics for control samples and cement samples obtained from downhole can be determined and used to account for variables in the control environment and the wellbore environment. For example, a control cement sample may have the same composition and be subjected to the same conditions as a cement sample obtained from downhole, but may exhibit slightly different material characteristics as a result of uncontrollable variables in either environment. By comparing the 3D mappings for control cement samples and downhole cement samples, a baseline relationship accounting for any offset of material characteristics can be determined.

For example, a slurry mixture may be set downhole under a given set of conditions and the same slurry mixture can be cured in a control environment under conditions as close to or the same as the conditions within the wellbore. The control sample may be slightly less porous than the cement sample from the drill cuttings. Multiple tests may show that multiple control cement samples have a less porous structure than the corresponding cement sample from downhole. By accounting for this expected offset, a desired slurry mixture can be selected, composed, or modified for various wellbore conditions based on the control cement sample(s). For example, the database can have information about control cement samples of various material characteristics at under various downhole conditions, and can be associated with a corresponding slurry mixture that will exhibit slightly more porous structures downhole than in a control environment. The cement analysis system 90 can take the difference in porosity between actual and control conditions into account to determine a best slurry mixture to be applied within the wellbore at those given downhole conditions and output this information to a user.

In some examples, the cement analysis system 90 can analyze the control cement samples to generate baseline 3D mappings representing material characteristics indicative of cement performance metrics, such as strength and permeability, for each cement sample. These control cement samples and wellbore cement samples may be cured at high temperatures, such as 230° F. (110° C.). The cement analysis system 90 can analyze control cement samples cured at high temperatures to generate the baseline 3D mappings and determine therefrom the strength and permeability of the control cement samples, which can indicate a strength retrogression of the control cement sample. The baseline 3D mappings for these control cement samples cured at high temperatures can used to compare against a 3D mapping of an actual cement sample from downhole to determine a strength retrogression of the cement sample.

In some examples, the database can include a cost of goods associated with each bulk blend material. The cement analysis system 90 can then apply linear (or non-linear) mathematical models to determine a slurry mixture with the lowest cost of goods in a specific wellbore application. In some examples, of these mathematical models can utilize compressive strength, tensile strength, Young's Modulus, Poisson's ratio, strain-to-failure, and American Society of Testing Materials ("ASTM") toughness. As one example, pozzolan may be attributed a cost per unit volume, and lime may be attributed a different cost per unit volume. The cement analysis system 90 can apply the mathematical models to information in the database (e.g., bulk blend components, crystalline phases, strength retrogression, and/or a cost of goods value for each bulk blend component) to determine a least costly slurry mixture of pozzolan and lime that is capable of setting successfully under certain wellbore conditions.

Although discussed in various examples for ease of explanation, the database can include any number and combination of the content discussed above. For example, the database can include 3D mappings for spatial and physicochemical relationships between particles, 3D mappings for strength retrogression analysis, mathematical equations used for mapping time-dependent mechanical properties, and cost of goods for each bulk component, among other things.

In some examples, a 3D mapping for a single cement sample can include information corresponding to spatial and physicochemical relationships between particles, 3D mappings for strength retrogression analysis, and time-dependent mechanical properties, such that multiple 3D mappings do not need to be created to showcase the various material characteristics useable throughout various wellbore applications.

Now referring back to FIG. 2, in block 208, a cement mixture is prepared based on the material characteristic identified in block 206. For example, the material characteristic identified in block 206 can be determined to be suboptimal, or inherently defective for a given cement sample. So, another cement mixture can be prepared with better material characteristics, in view of the material characteristics of the cement sample. For example, a cement sample can be determined to have a weak structural integrity based on a low-density value. Based on an analysis of the cement sample, cement mixtures that are to be used in future applications can be composed to have a higher density value, where the higher density value is the result of adjusting one or more material characteristics of the cement mixture composition used to create the cement sample. In some examples, a remedial action can be performed to resolve any issues related to the cement from which the cement sample was obtained.

In some examples, the cement mixture can be prepared at least in part by modifying a composition of an existing cement mixture, for example, of a cement mixture being poured downhole. This can result in a modification of one or more material characteristics of the resulting set cement. In some examples, the composition of the cement mixture being poured downhole can be altered preemptively by a well operator based on baseline 3D mappings in the database, such that a given baseline 3D mapping can suggest which composition(s) of bulk blend components can be used to successfully set the cement downhole. As one specific example, additional silica can be added to the cement mixture. Silica can be added to cement mixtures in high-temperature environments to reduce the amount of strength retrogression exhibited by the cement during the curing process.

In some examples, the cement analysis system 90 can automatically modify the composition of the cement. For example, the cement analysis system 90 can control the mixture of bulk blend components being pumped downhole via one or more valves. The cement analysis system 90 can manipulate the valves to adjust the composition of the cement (e.g., as needed to meet certain desirable criteria). In some examples, the cement analysis system 90 can output information to a display device for an operator to use in determining a new or modified composition of a cement mixture based on the material characteristics of the cement samples.

In some examples, determining the material characteristics of a cement sample drilled out of a casing shoe can help determine the composition of bulk blend components and wellbore environmental conditions to apply for setting another casing string. If the cement in the casing shoe did not set correctly, the cement sample can be analyzed to determine the point of failure or any other points of improvement that may further reduce the risk of setting failure. For example, a cement sample drilled out of a casing shoe can be determined to be weak due to excess amounts of pozzolan, such that large amounts of unreacted pozzolan exist causing the cement to be fragile. Using this information, the cement analysis system 90 can determine a different cement mixture (e.g., with less pozzolan) to apply at the specific environmental conditions within the wellbore to reduce the chance for setting failure.

In some examples, a downhole condition of the wellbore can be modified to adjust a material characteristic of the cement being set. Modifying a downhole condition can include altering a temperature value, pressure value, length of time, or density value of or applied to curing cement. Curing duration can be determined as a function of time and shortened or lengthened, such that an identified material characteristic of the cement sample may improve as time progress. Density and pressure values can be modified by altering the downhole weight on the cement. For example, the weight on the cement poured downhole can be increased or decreased to adjust the pressure applied to the cement at the casing shoe. Altering the pressure on the cement can affect the density of the resulting set cement.

In some examples, various wellbore tools and apparatuses may be used to alter environmental conditions within the wellbore. The cement analysis system 90 can automatically (or at user direction) communicate with such tools and apparatuses to cause them to modify the downhole condition accordingly. In one example, the cement analysis system 90 can control a pressure value to modify downhole pressures in a particular manner to manipulate the density of the cement downhole as it cures.

In some examples, the cement analysis system 90 can determine the least costly slurry mixture automatically by using downhole or surface sensors to determine conditions within the wellbore. For example, a wellbore may have high pressure and temperature conditions, such that a slurry would need to maintain certain values for time-dependent mechanical properties to set successfully. Meeting those time-dependent mechanical properties requirements may only be achieved with certain types of bulk components and/or with certain amounts of those bulk components. Using the database including the baseline 3D mappings, the cement analysis system 90 can determine one or more slurry mixtures that can maintain those time-dependent mechanical properties values. As such, there may be more than one combination of slurry mixtures capable of producing the desired time-dependent mechanical properties to successfully set under the given wellbore conditions. The cement analysis system 90 can then use the cost of goods and mathematical models to determine which of the slurry mixtures capable of producing the desired time-dependent mechanical properties would result in the lowest operational cost or meet a threshold cost value for a given application. In some examples, a user operating the cement analysis system 90 may input one or more wellbore conditions and mechanical characteristics. Based on the wellbore conditions and mechanical characteristics input by the user, the cement analysis system 90 can output a particular composition of a slurry mixture having the lowest cost of goods possible or having a cost of goods beneath a certain threshold cost value.

As alluded to above, in some examples the cement analysis system 90 can be in wired or wireless communication with downhole well tools to transmit control signals including commands to alter operations of one or more well tools. The alterations to the operations of the well tools can modify the downhole conditions, which can affect one or more material characteristics of the cement during the curing process. In some examples, the cement analysis system 90 can identify a material characteristics contributing to cement setting problems and responsively can issue a notification to a graphical user interface or other display device to cause a wellbore operator to take some remedial action, such as adjusting a well tool or adjusting the composition of the cement mixture.

Figure 6:
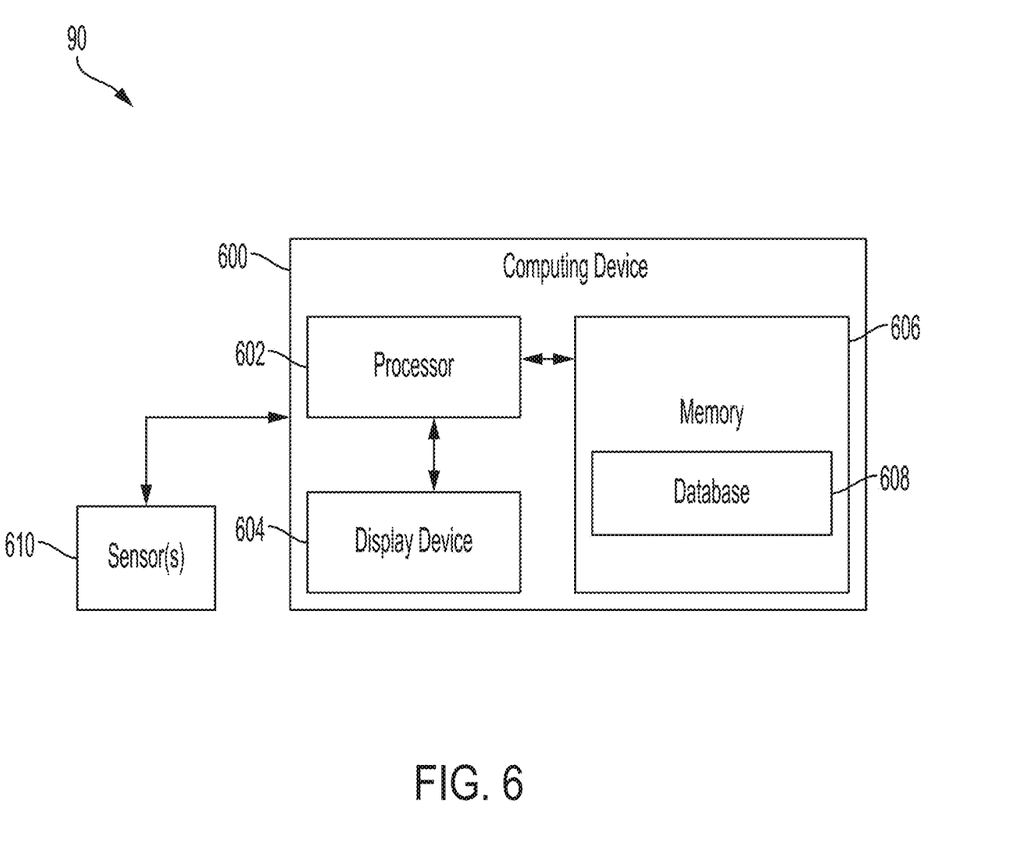
FIG. 6 is a block diagram of an example of a cement analysis system according to one aspect of the present disclosure.

FIG. 6 is a block diagram of a cement analysis system 90 according to some examples of the present disclosure. The cement analysis system 90 can include a computing device 600 having a processor 602, a display device 604, and a memory 606. In some examples, the components shown in FIG. 6 (e.g., the processor 602, the display device 604, and the memory 606) can be integrated into a single structure. For example, the components can be within a single housing. In other examples, the components shown in FIG. 6 can be distributed (e.g., in separate housings) and in electrical communication with each other.

Sensor(s) 610 can be communicatively coupled to the computing device 600 to transmit information about the downhole wellbore conditions and/or materials analyzed. Examples of the sensors 610 can include temperature, pressure, acoustic, geothermal, and other sensors useable to perform cement analysis techniques that are deployable via wireline, located in downhole tools, or within the cement analysis system 90. In some examples, the sensor(s) 610 can analyze bulk blend components and/or crystalline phases and transmit associated information to the computing device 600 for processing.

The processor 602 can execute one or more operations for implementing some examples. The processor 602 can execute instructions stored in the memory 606 to perform the operations. The processor 602 can include one processing device or multiple processing devices. Non-limiting examples of the processor 602 include a Field-Programmable Gate Array ("FPGA"), an application-specific integrated circuit ("ASIC"), a microprocessor, etc.

The processor 602 can be communicatively coupled to the memory 606 via a bus. The non-volatile memory 606 may include any type of memory device that retains stored information when powered off. Non-limiting examples of the memory 606 include electrically erasable and programmable read-only memory ("EEPROM"), flash memory, or any other type of non-volatile memory. In some examples, at least some of the memory 606 can include a medium from which the processor 602 can read instructions. A computer-readable medium can include electronic, optical, magnetic, or other storage devices capable of providing the processor 602 with computer-readable instructions or other program code. Non-limiting examples of a computer-readable medium include (but are not limited to) magnetic disk(s), memory chip(s), ROM, RAM, an ASIC, a configured processor, optical storage, or any other medium from which a computer processor can read instructions. The instructions can include processor-specific instructions generated by a compiler or an interpreter from code written in any suitable computer-programming language, including, for example, C, C++, C#, etc.

The memory 606 can include a database 608, which can include any amount and combination of the content described in previous examples. The database 608 can store 3D mappings for spatial and physicochemical relationships between particles, 3D mappings for strength retrogression analysis, mathematical equations used for mapping time-dependent mechanical properties, cost of goods for each bulk component, or any combination of these, among other things.

The display device 604 can receive display signals from the processor 602 and responsively output any information related to the 3D mappings, time-dependent material characteristics, notifications to take remedial action, or any other information useable to manage wellbore cement compositions based on material characteristics. One example of the display device 604 can include a liquid crystal display.

In some aspects, systems, devices, and methods for managing wellbore cement compositions based on material characteristics are provided according to one or more of the following examples:

Example #1: A method can include retrieving a cement sample from a wellbore. The method can include analyzing the cement sample using a plurality of sensors to generate a three-dimensional mapping of particles in the cement sample, the three-dimensional mapping representing three-dimensional spatial relationships between the particles in the cement sample. The method can include comparing the three-dimensional mapping to a plurality of baseline three-dimensional mappings in a database to identify at least one material characteristic of the cement sample. The method can include preparing a cement mixture (e.g., usable at a future point in time) based on the at least one material characteristic of the cement sample from the wellbore.

Example #2: The method of Example #1 may feature the cement sample being a cement cutting from a casing shoe. The plurality of sensors can include any combination of: a first sensor configured to perform X-Ray Computing Tomography on the cement sample, a second sensor configured to perform Focused Ion-Beam Scanning Electron Macroscopy with X-Ray Diffraction on the cement sample, a third sensor configured to perform X-Ray Fluorescence on the cement sample, a fourth sensor configured to perform Energy Dispersive Spectroscopy on the cement sample, or a fifth sensor configured to perform Nuclear Magnetic Resonance on the cement sample.

Example #3: The method of any of Examples #1-2 may feature the at least one material characteristic comprising one or more physical properties selected from the group consisting of: a porosity of the cement sample, density of the cement sample, CSH content in the cement sample, degree of crystallinity, a volume fraction of a chemical component in the cement sample, a total surface area of a chemical component in the cement sample, a given geometric shape factor of a chemical component in the cement sample, and an amount of unreacted bulk blend component in the cement sample.

Example #4: The method of any of Examples #1-3 may involve the database being generated by: preparing a plurality of slurry mixtures; curing the plurality of slurry mixtures under combinations of conditions including temperature values, pressure values, time values, and density values to create baseline cement samples; and analyzing the baseline cement samples using the plurality of sensors to generate the plurality of baseline three-dimensional mappings.

Example #5: The method of any of Examples #1-4 may feature the temperature values being greater than or equal to 230° F. (110° C.). The plurality of baseline three-dimensional mappings can describe strength and permeability characteristics for each of the baseline cement samples.

Example #6: The method of any of Examples #1-5 may feature the at least one material characteristic comprising one or more mechanical properties selected from the group consisting of: a Young's modulus, a Poisson's ratio, strain to failure, compressive toughness, a compressive strength, and a tensile strength of the cement sample.

Example #7: The method of Example #6 may feature the one or more mechanical properties being time-dependent mechanical properties.

Example #8: The method of any of Examples #1-7 may involve determining that a cost of the cement mixture is less than a threshold cost value using information in a database; determining that the cement mixture has a particular composition associated with the at least one material characteristic of the cement sample using the information in the database; and in response to determining that (i) the cost of the cement mixture is less than the threshold cost value and (ii) the cement mixture has the particular composition associated with the at least one material characteristic, preparing the cement mixture to have the particular composition.

Example #9: A system can include a plurality of sensors configured to detect a plurality of characteristics of a cement sample obtained from a wellbore and transmit sensor signals representing the plurality of characteristics. The sensor can include a processing device communicatively coupled to the plurality of sensors. The System can include a memory device comprising instructions that are executable by the processing device for causing the processing device to perform operations. The operations can include receiving the sensor signals from the plurality of sensors; generating a three-dimensional mapping of particles in the cement sample based on the sensor signals, the three-dimensional mapping representing three-dimensional spatial relationships between the particles in the cement sample; comparing the three-dimensional mapping to a plurality of baseline three-dimensional mappings in a database to identify at least one material characteristic of the cement sample; and outputting information usable for preparing a cement mixture (e.g., at a future point in time) based on the at least one material characteristic of the cement sample from the wellbore.

Example #10: The system of Example #9 may feature the cement sample being a cement cutting from a casing shoe. The plurality of sensors can include any combination of: a first sensor configured to perform X-Ray Computing Tomography on the cement sample, a second sensor configured to perform Focused Ion-Beam Scanning Electron Macroscopy with X-Ray Diffraction on the cement sample, a third sensor configured to perform X-Ray Fluorescence on the cement sample, a fourth sensor configured to perform Energy Dispersive Spectroscopy on the cement sample, or a fifth sensor configured to perform Nuclear Magnetic Resonance on the cement sample.

Example #11: The system of any of Examples #9-10 may feature the at least one material characteristic comprising one or more physical properties selected from the group consisting of: a porosity of the cement sample, density of the cement sample, CSH content in the cement sample, degree of crystallinity, a volume fraction of a chemical component in the cement sample, a total surface area of a chemical component in the cement sample, a given geometric shape factor of a chemical component in the cement sample, and an amount of unreacted bulk blend component in the cement sample.

Example #12: The system of any of Examples #9-11 may feature the memory device further comprising instructions that are executable by the processing device for causing the processing device to generate the database by analyzing baseline cement samples prepared under a plurality of temperature values using the plurality of sensors to generate the plurality of baseline three-dimensional mappings.

Example #13: The system of any of Examples #9-12 may feature the plurality of temperature values being greater than or equal to 230° F. (110° C.). The plurality of baseline three-dimensional mappings can describe strength and permeability characteristics for each of the baseline cement samples.

Example #14: The system of any of Examples #9-13 may feature the at least one material characteristic comprising one or more mechanical properties selected from the group consisting of: a Young's modulus, a Poisson's ratio, a compressive strength, strain to failure, compressive toughness, and a tensile strength of the cement sample.

Example #15: The system of Example #14 may feature the one or more mechanical properties being time-dependent mechanical properties.

Example #16: The system of any of Examples #9-15 may feature the memory device further comprising instructions that are executable by the processing device for causing the processing device to: determine that a cost of the cement mixture is less than a threshold cost value using information in a database; determine that the cement mixture has a particular composition associated with the at least one material characteristic of the cement sample using the information in the database; and in response to determining that (i) the cost of the cement mixture is less than the threshold cost value and (ii) the cement mixture has the particular composition associated with the at least one material characteristic, configure the information to indicate that the cement mixture is to have the particular composition.

Example #17: A non-transitory computer-readable medium comprising program code that is executable by a processing device for causing the processing device to: receive sensor signals from a plurality of sensors, the sensor signals representing a plurality of characteristics of a cement sample obtained from a wellbore; generate a three-dimensional mapping of particles in the cement sample based on the sensor signals, the three-dimensional mapping representing three-dimensional spatial relationships between the particles in the cement sample; compare the three-dimensional mapping to a plurality of baseline three-dimensional mappings in a database to identify at least one material characteristic of the cement sample; and output information usable for preparing a cement mixture (e.g., at a future point in time) based on the at least one material characteristic of the cement sample from the wellbore.

Example #18: The non-transitory computer-readable medium of Example #17 may feature the cement sample being a cement cutting from a casing shoe. The plurality of sensors include any combination of: a first sensor configured to perform X-Ray Computing Tomography on the cement sample, a second sensor configured to perform Focused Ion-Beam Scanning Electron Macroscopy with X-Ray Diffraction on the cement sample, a third sensor configured to perform X-Ray Fluorescence on the cement sample, a fourth sensor configured to perform Energy Dispersive Spectroscopy on the cement sample, or a fifth sensor configured to perform Nuclear Magnetic Resonance on the cement sample.

Example #19: The non-transitory computer-readable medium of any of Examples #17-18 may feature the at least one material characteristic comprising one or more physical properties selected from the group consisting of: a porosity of the cement sample, density of the cement sample, CSH content in the cement sample, degree of crystallinity, a volume fraction of a chemical component in the cement sample, a total surface area of a chemical component in the cement sample, a given geometric shape factor of a chemical component in the cement sample, and an amount of unreacted bulk blend component in the cement sample.

Example #20: The non-transitory computer-readable medium of any of Examples #17-19 may feature program code that is executable by the processing device for causing the processing device to: determine that a cost of the cement mixture is less than a threshold cost value using information in a database; determine that the cement mixture has a particular composition associated with the at least one material characteristic of the cement sample using the information in the database; and in response to determining that (i) the cost of the cement mixture is less than the threshold cost value and (ii) the cement mixture has the particular composition associated with the at least one material characteristic, configure the information to indicate that the cement mixture is to have the particular composition.

The foregoing description of certain examples, including illustrated examples, has been presented only for the purpose of illustration and description and is not intended to be exhaustive or to limit the disclosure to the precise forms disclosed. Numerous modifications, adaptations, and uses thereof will be apparent to those skilled in the art without departing from the scope of the disclosure.

What is claimed is:

1. A method comprising:
   retrieving a cement sample from a wellbore;
   analyzing the cement sample using a plurality of sensors to generate a three-dimensional mapping of particles in the cement sample, the three-dimensional mapping representing three-dimensional spatial relationships between the particles in the cement sample;
   comparing the three-dimensional mapping to a plurality of baseline three-dimensional mappings in a database to identify at least one material characteristic of the cement sample; and
   preparing a cement mixture based on the at least one material characteristic of the cement sample from the wellbore.

2. The method of claim 1, wherein:
   the cement sample is a cement cutting from a casing shoe; and
   the plurality of sensors include any combination of: a first sensor configured to perform X-Ray Computing Tomography on the cement sample, a second sensor configured to perform Focused Ion-Beam Scanning Electron Macroscopy with X-Ray Diffraction on the cement sample, a third sensor configured to perform X-Ray Fluorescence on the cement sample, a fourth sensor configured to perform Energy Dispersive Spectroscopy on the cement sample, or a fifth sensor configured to perform Nuclear Magnetic Resonance on the cement sample.

3. The method of claim 1, wherein the at least one material characteristic comprises one or more physical properties selected from the group consisting of: a porosity of the cement sample, density of the cement sample, CSH content in the cement sample, degree of crystallinity, a volume fraction of a chemical component in the cement sample, a total surface area of a chemical component in the cement sample, a given geometric shape factor of a chemical component in the cement sample, and an amount of unreacted bulk blend component in the cement sample.

4. The method of claim 1, further comprising generating the database by:
preparing a plurality of slurry mixtures;
curing the plurality of slurry mixtures under combinations of conditions including temperature values, pressure values, time values, and density values to create baseline cement samples; and
analyzing the baseline cement samples using the plurality of sensors to generate the plurality of baseline three-dimensional mappings.

5. The method of claim 4, wherein the temperature values are greater than or equal to 230° F. (110° C.), and wherein the plurality of baseline three-dimensional mappings describe strength and permeability characteristics for each of the baseline cement samples.

6. The method of claim 1, wherein the at least one material characteristic comprises one or more mechanical properties selected from the group consisting of: a Young's modulus, a Poisson's ratio, strain to failure, compressive toughness, a compressive strength, and a tensile strength of the cement sample.

7. The method of claim 6, wherein the one or more mechanical properties are time-dependent mechanical properties.

8. The method of claim 1, further comprising:
determining that a cost of the cement mixture is less than a threshold cost value using information in a database;
determining that the cement mixture has a particular composition associated with the at least one material characteristic of the cement sample using the information in the database; and
in response to determining that (i) the cost of the cement mixture is less than the threshold cost value and (ii) the cement mixture has the particular composition associated with the at least one material characteristic, preparing the cement mixture to have the particular composition.

9. A system comprising:
a plurality of sensors configured to detect a plurality of characteristics of a cement sample obtained from a wellbore and transmit sensor signals representing the plurality of characteristics;
a processing device communicatively coupled to the plurality of sensors; and
a memory device comprising instructions that are executable by the processing device for causing the processing device to:
receive the sensor signals from the plurality of sensors;
generate a three-dimensional mapping of particles in the cement sample based on the sensor signals, the three-dimensional mapping representing three-dimensional spatial relationships between the particles in the cement sample;
compare the three-dimensional mapping to a plurality of baseline three-dimensional mappings in a database to identify at least one material characteristic of the cement sample; and
output information usable for preparing a cement mixture based on the at least one material characteristic of the cement sample from the wellbore.

10. The system of claim 9, wherein:
the cement sample is a cement cutting from a casing shoe; and
the plurality of sensors include any combination of: a first sensor configured to perform X-Ray Computing Tomography on the cement sample, a second sensor configured to perform Focused Ion-Beam Scanning Electron Macroscopy with X-Ray Diffraction on the cement sample, a third sensor configured to perform X-Ray Fluorescence on the cement sample, a fourth sensor configured to perform Energy Dispersive Spectroscopy on the cement sample, or a fifth sensor configured to perform Nuclear Magnetic Resonance on the cement sample.

11. The system of claim 9, wherein the at least one material characteristic comprises one or more physical properties selected from the group consisting of: a porosity of the cement sample, density of the cement sample, CSH content in the cement sample, degree of crystallinity, a volume fraction of a chemical component in the cement sample, a total surface area of a chemical component in the cement sample, a given geometric shape factor of a chemical component in the cement sample, and an amount of unreacted bulk blend component in the cement sample.

12. The system of claim 9, the memory device further comprising instructions that are executable by the processing device for causing the processing device to generate the database by:
analyzing baseline cement samples prepared under a plurality of temperature values using the plurality of sensors to generate the plurality of baseline three-dimensional mappings.

13. The system of claim 12, wherein the plurality of temperature values are greater than or equal to 230° F. (110° C.), and wherein the plurality of baseline three-dimensional mappings describe strength and permeability characteristics for each of the baseline cement samples.

14. The system of claim 9, wherein the at least one material characteristic comprises one or more mechanical properties selected from the group consisting of: a Young's modulus, a Poisson's ratio, a compressive strength, strain to failure, compressive toughness, and a tensile strength of the cement sample.

15. The system of claim 14, wherein the one or more mechanical properties are time-dependent mechanical properties.

16. The system of claim 9, the memory device further comprising instructions that are executable by the processing device for causing the processing device to:
determine that a cost of the cement mixture is less than a threshold cost value using information in a database;
determine that the cement mixture has a particular composition associated with the at least one material characteristic of the cement sample using the information in the database; and
in response to determining that (i) the cost of the cement mixture is less than the threshold cost value and (ii) the cement mixture has the particular composition associated with the at least one material characteristic, configure the information to indicate that the cement mixture is to have the particular composition.

17. A non-transitory computer-readable medium comprising program code that is executable by a processing device for causing the processing device to:
   receive sensor signals from a plurality of sensors, the sensor signals representing a plurality of characteristics of a cement sample obtained from a wellbore;
   generate a three-dimensional mapping of particles in the cement sample based on the sensor signals, the three-dimensional mapping representing three-dimensional spatial relationships between the particles in the cement sample;
   compare the three-dimensional mapping to a plurality of baseline three-dimensional mappings in a database to identify at least one material characteristic of the cement sample; and
   output information usable for preparing a cement mixture based on the at least one material characteristic of the cement sample from the wellbore.

18. The non-transitory computer-readable medium of claim 17, wherein:
   the cement sample is a cement cutting from a casing shoe; and
   the plurality of sensors include any combination of: a first sensor configured to perform X-Ray Computing Tomography on the cement sample, a second sensor configured to perform Focused Ion-Beam Scanning Electron Macroscopy with X-Ray Diffraction on the cement sample, a third sensor configured to perform X-Ray Fluorescence on the cement sample, a fourth sensor configured to perform Energy Dispersive Spectroscopy on the cement sample, or a fifth sensor configured to perform Nuclear Magnetic Resonance on the cement sample.

19. The non-transitory computer-readable medium of claim 17, wherein the at least one material characteristic comprises one or more physical properties selected from the group consisting of: a porosity of the cement sample, density of the cement sample, CSH content in the cement sample, degree of crystallinity, a volume fraction of a chemical component in the cement sample, a total surface area of a chemical component in the cement sample, a given geometric shape factor of a chemical component in the cement sample, and an amount of unreacted bulk blend component in the cement sample.

20. The non-transitory computer-readable medium of claim 17, further comprising program code that is executable by the processing device for causing the processing device to:
   determine that a cost of the cement mixture is less than a threshold cost value using information in a database;
   determine that the cement mixture has a particular composition associated with the at least one material characteristic of the cement sample using the information in the database; and
   in response to determining that (i) the cost of the cement mixture is less than the threshold cost value and (ii) the cement mixture has the particular composition associated with the at least one material characteristic, configure the information to indicate that the cement mixture is to have the particular composition.

* * * * *